United States Patent [19]

Behr et al.

[11] Patent Number: 5,321,156
[45] Date of Patent: Jun. 14, 1994

[54] PROCESS FOR PREPARING ALKALI METAL SALTS OF 3-HYDROXYPROPIONIC ACID

[75] Inventors: Arno Behr, Duesseldorf; Andreas Botulinski, Dormagen; Franz-Josef Carduck, Haan; Michael Schneider, Velbert, all of Fed. Rep. of Germany

[73] Assignee: Henkel Kommanditgesellschaft auf Aktien, Duesseldorf, Fed. Rep. of Germany

[21] Appl. No.: 117,093
[22] PCT Filed: Mar. 4, 1992
[86] PCT No.: PCT/EP92/00477
§ 371 Date: Sep. 13, 1993
§ 102(e) Date: Sep. 13, 1993
[87] PCT Pub. No.: WO92/16489
PCT Pub. Date: Oct. 1, 1992

[30] Foreign Application Priority Data

Mar. 13, 1991 [DE] Fed. Rep. of Germany ....... 4107987

[51] Int. Cl.$^5$ .............................................. C07C 51/16
[52] U.S. Cl. .................................................... 562/538
[58] Field of Search ................ 562/538, 543, 546, 567

[56] References Cited

U.S. PATENT DOCUMENTS

| | | | |
|---|---|---|---|
| 3,897,489 | 7/1975 | Sheng | 260/531 |
| 4,082,788 | 4/1978 | Mims | 562/543 X |
| 4,296,242 | 10/1981 | Nagabhushan et al. | 562/567 X |
| 4,435,598 | 3/1984 | Hinnenkamp | 562/546 |

FOREIGN PATENT DOCUMENTS 1035639 8/1958 Fed. Rep. of Germany .
56-05433 1/1981 Japan .

OTHER PUBLICATIONS

Chemical Abstracts, vol. 86, No. 13, Mar. 28, 1977, Columbus, Ohio; Abstract No. 89185k.

*Primary Examiner*—Arthur C. Prescott
*Attorney, Agent, or Firm*—Ernest G. Szoke; Wayne C. Jaeschke; Norvell E. Wisdom, Jr.

[57] ABSTRACT

By reacting 1,3-propanediol with oxygen or an oxygen-containing gas in an aqueous alkaline solution in the presence of a palladium containing catalyst substrate, alkaline salts of 3-hydroxypropionic acid are produced in good yield when the catalyst is used in an amount that corresponds to 0.1 to 3.0% by weight of palladium, based on the 1,3-propanediol.

6 Claims, No Drawings

PROCESS FOR PREPARING ALKALI METAL SALTS OF 3-HYDROXYPROPIONIC ACID

FIELD OF THE INVENTION

This invention relates to a process for the production of alkali metal salts of 3-hydroxypropionic acid by oxidation of propane-1,3-diol in aqueous alkaline solution in the presence of a palladium catalyst.

STATEMENT OF RELATED ART

3-Hydroxypropionic acid and its salts are valuable building blocks in organic synthesis. 3-Hydroxypropionic acid is normally prepared by addition of water onto acrylic acid or by reaction of ethylene chlorohydrin with sodium cyanide and subsequent hydrolysis of the β-propiolactone formed [*Ullmann's Encyclopoedia of Industrial Chemistry*, 5th Edition, Vol. A-13, pages 507–517]. Both processes involve the handling of toxic substances. Accordingly, a search was made for a process by which toxicologically safe propane-1,3-diol, which can readily be obtained in high yields from glycerol by fermentation, could be converted by oxidation into 3-hydroxypropionic acid or alkali metal salts thereof.

The oxidation of propane-1,3-diol, hereinafter referred to in brief as diol, in presence of a noble metal catalyst is known from the literature. Thus, published Japanese patent application JP 56/5433 (Sanyo) claims a process for the production of malonic acid by reaction of propane-1,3-diol with oxygen or an oxygen-containing gas. The process is preferably carried out in the presence of a platinum group catalyst. According to the Sanyo application, malonic acid can be obtained in high yields using 3.3% by weight palladium, based on the diol.

DESCRIPTION OF THE INVENTION

Object of the Invention

The problem addressed by the present invention was to provide a process by which propane-1,3-diol could be oxidized in high yields to 3-hydroxypropionic acid.

Summary of the Invention

According to the invention, this problem has been solved by a process for the production of an alkali metal salt of 3-hydroxypropionic acid by reaction of propane-1,3-diol with oxygen or an oxygen-containing gas in aqueous alkaline solution in the presence of a palladium-containing supported catalyst, characterized in that the catalyst is used in a quantity corresponding to 0.1 to 3.0% by weight of palladium, based on propane-1,3-diol.

Description of the Preferred Embodiments

Palladium on a solid support, for example active carbon or aluminum oxide, is used as the catalyst, the quantity of palladium in the catalyst being from 0.5 to 10% by weight and preferably from 2 to 5% by weight, based on the support.

The practicability of the process according to the invention is attributable to the fact that the predominant formation of 3-hydroxypropionic acid (selective oxidation of propane-1,3-diol) takes priority over the competitive formation of malonic acid (complete oxidation of propane-1,3-diol) where the low catalyst concentration according to the invention, based on the diol, is used.

In one preferred embodiment of the invention, the quantity of palladium present in the catalyst, based on propane-1,3-diol, is between 0.1 and 1.0% by weight.

It has been found that high yields of 3-hydroxypropionic acid are obtained even when, over and above the palladium present, the catalyst additionally contains platinum and/or bismuth. The total quantity of platinum and/or bismuth should be at most twice the quantity by weight of palladium. Particularly good results have been obtained with a catalyst containing 4% by weight of palladium, 1% by weight of platinum and 5% by weight of bismuth on powdered active carbon.

The catalyst is normally activated before use. This is readily done by dispersing the catalyst in water and subsequently contacting it with inert gases, for example hydrogen and/or nitrogen, to displace adhering oxygen.

The catalyst may be repeatedly reused in the process according to the invention without any losses of yield having to be accepted. On the contrary, it has even been found that the catalyst only develops its full activity after it has been used at least once to three times.

The concentration of the diol in the reaction mixture is not subject to any particular limitations, although a concentration of 5 to 20% by weight is preferred. It is of particular advantage in this regard to adjust the concentration of the diol in the reaction mixture to a value of 6 to 12% by weight and, more particularly, to a value of 8 to 10% by weight. In this case, the quantity of palladium present in the catalyst can be further reduced to 0.1 to 0.3% by weight of the same high yield.

According to the invention, the oxidation of propane-1,3-diol is carried out in alkaline medium. In this way, the 3-hydroxypropionic acid formed is neutralized and thus protected against partial yield-reducing degradation by decarboxylation. The pH value of the aqueous alkaline reaction mixtures should be in the range from 8 to 13 and is preferably in the range from 9 to 12. Particularly good results are obtained at pH values of 10 to 11.

Oxidation of the diol is carried out at a constant pH value of the reaction mixture throughout the reaction. The constant pH value may be controlled, for example, by coupling a pH meter, which continuously monitors the pH value of the reaction mixture, to a metering unit containing the corresponding alkali metal hydroxide. The alkali metal hydroxides used are preferably sodium hydroxide and potassium hydroxide, more particularly in the form of aqueous solutions. The concentration of the aqueous alkali metal hydroxide used is not subject to any particular limitation, although it is clear that the use of highly dilute solutions is uneconomical in regard to optimal utilization of the reactor. For practical reasons, therefore, 20 to 50% by weight of aqueous alkali metal hydroxides will be used. In the case of NaOH, it has proved to be practical to use a 30% by weight, i.e. 10-normal, solution.

In the process according to the invention, oxidation of the diol is preferably carried out at temperatures of 40° to 55° C. Higher temperatures do not produce any significant increases in yield and actually involve the danger of dehydration of the 3-hydroxypropionic acid to acrylic acid.

In the process according to the invention, the reaction mixture is contacted with oxygen or an oxygen-containing gas, for example air. This may readily be done, for example, by injecting air into the reaction mixture with stirring. It has been found that a flow rate of 30 normal liters of air per hour, based on 700 to 1000 ml reaction mixture, is particularly suitable. At lower flow rates, for example 10 normal liters air per hour, the reaction time is significantly extended and the reaction mixture can undergo unwanted yellowing; at higher flow rates, the removal of catalyst from the reactor is too high.

The reaction may be carried out under pressures of 1.0 to 1.5 bar, but is preferably carried out under a slight excess pressure of the order of 1.01 to 1.06 bar.

In kinetic studies, it was found that the consumption of alkali metal hydroxide in the process according to the invention is dependent on time. The consumption of alkali metal hydroxide initially increases linearly as a function of time, reaching a plateau value at the end of the reaction. On the basis of this observation, therefore, the end point of the reaction may readily be determined from the fact that no more alkali metal hydroxide is needed to keep the pH value constant. At this stage, the reaction is terminated and the reaction mixture is worked up in the usual way beginning with removal of the catalyst by filtration.

The alkali metal salt of 3-hydroxypropionic acid obtained may be used either directly or after further concentration in the form of an aqueous solution. If desired, the alkali metal salt may be converted by acidification, for example by means of an acidic ion exchanger, into the free 3-hydroxypropionic acid, which may optionally be purified by distillation.

The following Examples are intended to illustrate the invention.

Examples

1. Reagents

The following catalysts were used:

a) 5% by weight Pd on active carbon with a water content of 52.5% by weight, commercially available under the name of Escat 10 (Engelhard).

b) 4% by weight Pd, 1% by weight Pt and 5% by weight Bi on active carbon with a water content of 59.3% by weight, commercially available under the name of Cef 196 raw (Degussa AG).

2. Test apparatus

The oxidations were carried out in a 2 liter pressure autoclave equipped with a turbine stirrer [1400 revolutions per minute]. Air and 30% by weight sodium hydroxide were introduced into the reaction mixture from below. NaOH was continuously introduced at such a rate that the pH value of the mixture remained constant. The pH was controlled through a metering dispenser (Dulcometer, manufacturer: Prominent) equipped with a resistance thermometer (Pt-100). The waste gas passed through a cooler (deposition of condensate), a buffer vessel, a water-filled washing bottle, a drying tower, a throughflow meter and an oxygen analyzer (Servomex 570, manufacturer: Bühler). Due to variations in air pressure, the instrument was recalibrated before each test. The consumption of oxygen was continuously recorded as a function of time by a connected recorder. The air throughput was adjusted by a precision control valve to a value of 30 normal liters per hour. The pressure inside the reactor was 1.06 bar.

3. Test descriptions

The quantities of catalyst shown in all the Examples and Comparison Examples are based on dry matter.

Example 1 (E1)

2.13 g of catalyst (Escat 10) were dispersed in 300 ml of water and activated overnight under hydrogen, a quantity of about 350 ml being taken up. The prepared catalyst was transferred to the autoclave together with 77.6 g (1 mole) of propane-1,3-diol and another 500 ml water. The autoclave was closed and the reaction mixture was heated under nitrogen to 50° C. The reaction was initiated by the simultaneous introduction of sodium hydroxide and air. NaOH was continuously introduced at such a rate that the pH value remained constant at 11. The air throughput was 30 normal liters per hour. As soon a constant value had been reached for the total amount of sodium hydroxide solution introduced as well as for the therewith connected total consumption of oxygen, the reaction was terminated, the reaction mixture was drained off by blowing out the NaOH feed line, and the yield was determined by weighing. After cooling of the mixture, the catalyst was filtered off through a suction filter and the samples were analyzed by HPLC (Shodex Ionpak C-811: cation exchange phase, 0.1% by weight aqueous phosphoric acid as eluent, Ri detection). The yields of 3-hydroxypropionic acid [in % of the theoretical] are shown together with other data in line 1 of Table 1.

TABLE 1

| Ex. | Propane-1,3-diol [g] | [mmoles] | Water [g] | Cat.[a] [g] | Pd[b] [%] | Temp. [°C.] | Time[c] [mins.] | Yield[d] [%] |
|---|---|---|---|---|---|---|---|---|
| E1 | 77.6 | 1000 | 800 | 2.13 | 0.14 | 50 | 1075[e] | 70.1 |
| E2 | 77.6 | 1000 | 800 | 3.80 | 0.24 | 50 | 490 | 74.7 |
| E3 | 77.6 | 1000 | 800 | 5.32 | 0.34 | 50 | 415 | 68.4 |
| E4 | 77.6 | 1000 | 800 | 10.64 | 0.69 | 50 | 330 | 51.5 |
| C1 | 77.6 | 1000 | 800 | 21.28 | 1.37 | 50 | 580 | 23.5 |
| E5 | 23.3 | 300 | 700 | 13.10 | 2.81 | 40 | 190 | 65.6 |
| C2 | 23.3 | 300 | 700 | 13.10 | 2.81 | 60 | 220 | 29.0 |

[a]Escat 10; the quantities of catalyst shown are dry weights
[b]% by weight palladium, based on propane-1,3-diol
[c]Reaction time in minutes
[d]Yield of 3-hydroxypropionic acid in % of the theoretical
[e]Air throughput: 10 normal liters per hour

Examples 2 to 4 (E2 to E4)

Example 1 was repeated with different quantities of catalyst. The results are set out in Table 1. It can be seen that optimal yields of 3-hydroxypropionic acid are obtained in particular at low catalyst concentrations.

Comparison Example 1 (C1)

Example 1 was repeated with a distinctly larger quantity of catalyst. Particulars are set out in Table 1. It can be seen that the increase in the quantity of catalyst is accompanied by a drastic reduction in the yield of 3-hydroxypropionic acid.

Example 5 (E5)

13.1 kg of catalyst (Escat 10) were dispersed in 300 ml of water and activated overnight under hydrogen, a quantity of about 900 ml being taken up. The prepared catalyst was transferred to the autoclave together with 23.3 g (300 mmoles) of propane-1,3-diol and another 400 ml of water. The autoclave was closed and the reaction mixture was heated under nitrogen to 40° C. The remaining procedure was as in Example 1. The yield of 3-hydroxypropionic acid was 65.6%, cf. Table 1.

Comparison Example 2 (C2)

Example 5 was repeated at 60° C. The yield of 3-hydroxypropionic acid was 29%, cf. Table 1.

Example 6 (E6)

13.1 kg of catalyst (Cef 196 raw) were dispersed in 300 ml of water and activated overnight under hydrogen, a quantity of about 900 ml being taken up. The prepared catalyst was transferred to the autoclave together with 31.1 g (400 mmoles) of propane-1,3-diol and another 631 ml of water. The autoclave was closed and the reaction mixture was heated under nitrogen to 50° C. The remaining procedure was as in Example 1. The yield of 3-hydroxypropionic acid was 81.8%, cf. Table 2.

Example 7 to 10 (E7 to E10)

Example 6 was repeated with different concentrations of propane-1,3-diol in the reaction mixture and hence indirectly with different ratios of catalyst to diol. Particulars and also the yields of 3-hydroxypropionic acid are set out in Table 2.

TABLE 2

| Ex. | Propane-1,3-diol [g] | [mmoles] | Water [g] | Cat.[a] [g] | Pd[b] [%] | Met[c] [%] | Temp. [°C.] | Time[d] [mins.] | Yield[e] [%] |
|---|---|---|---|---|---|---|---|---|---|
| E6 | 31.1 | 400 | 931 | 17.46 | 2.2 | 3.4 | 50 | 140 | 81.8 |
| E7 | 23.3 | 300 | 700 | 13.10 | 2.3 | 3.3 | 50 | 140 | 73.8 |
| E8 | 46.6 | 600 | 700 | 13.10 | 1.1 | 1.7 | 50 | 240 | 77.2 |
| E9 | 69.8 | 900 | 700 | 13.10 | 0.8 | 1.1 | 50 | 300 | 78.2 |
| E10 | 93.1 | 1200 | 700 | 13.10 | 0.6 | 0.8 | 50 | 570 | 70.5 |

[a] Cef 196 raw; the quantities of catalyst shown are dry weights
[b] % by weight palladium, based on propane-1,3-diol
[c] % by weight platinum + bismuth (based on propane-1,3-diol
[d] Reaction time in minutes
[e] Yield of 3-hydroxypropionic acid in % of the theoretical

The invention claimed is:

1. A process for the production of an alkali metal salt of 3-hydroxypropionic acid by reaction of propane-1,3-diol with oxygen or an oxygen-containing gas in aqueous alkaline solution in the presence of a palladium-containing supported catalyst, wherein:
   (a) the catalyst is used in a quantity corresponding to 0.1 to 3.0% by weight of palladium, based on propane-1,3-diol and
   (b) the reaction is carried out at a temperature of 40° to 55° C.

2. A process as claimed in claim 1, wherein the catalyst is used in a quantity corresponding to 0.1 to 1.0% by weight of palladium, based on propane-1,3-diol.

3. A process as claimed in claim 2, wherein propane-1,3-diol is used in a quantity corresponding to 6 to 12% by weight, based on the reaction mixture.

4. A process as claimed in claim 3, wherein the catalyst is used in a quantity corresponding to 0.1 to 0.3% by weight of palladium, based on propane-1,3-diol.

5. A process as claimed in claim 1, wherein a catalyst additionally containing platinum, bismuth, or both platinum and bismuth is used.

6. A process as claimed in claim 5, wherein a catalyst containing 4% by weight of palladium, 1% by weight of platinum and 5% by weight of bismuth is used.

* * * * *